United States Patent
Eltomi et al.

(10) Patent No.: US 7,833,481 B2
(45) Date of Patent: Nov. 16, 2010

(54) FULLY INTEGRATED PORTABLE SCREENING SYSTEM

(75) Inventors: Khaled F. Eltomi, Rockville, MD (US); Jack Kotowicz, Washington, DC (US); Pratheev Sabaratnam Sreetharan, Bethesda, MD (US); Regina Elvira Dugan, Rockville, MD (US)

(73) Assignee: RedXDefense, LLC, Rockville, MD (US)

( * ) Notice: Subject to any disclaimer, the term of this patent is extended or adjusted under 35 U.S.C. 154(b) by 895 days.

(21) Appl. No.: 11/525,509

(22) Filed: Sep. 22, 2006

(65) Prior Publication Data
US 2010/0240143 A1   Sep. 23, 2010

Related U.S. Application Data

(60) Provisional application No. 60/723,433, filed on Oct. 5, 2005.

(51) Int. Cl.
*G01N 7/00* (2006.01)
*G01N 21/00* (2006.01)
*G01N 33/00* (2006.01)

(52) U.S. Cl. ............................. 422/83; 422/56; 422/57; 422/58; 422/84; 422/85; 422/86; 422/87; 422/88; 436/92; 436/110; 436/901; 73/23.2; 73/23.3; 73/23.4; 73/29.01

(58) Field of Classification Search ........................ None
See application file for complete search history.

(56) References Cited

U.S. PATENT DOCUMENTS

| | | | |
|---|---|---|---|
| 4,019,863 A * | 4/1977 | Jenkins et al. ............... 250/304 |
| 4,788,039 A | 11/1988 | Glattstein | |
| 4,983,058 A * | 1/1991 | Nagae ........................ 400/249 |
| 5,035,860 A * | 7/1991 | Kleingeld et al. ............. 422/61 |
| 5,109,691 A * | 5/1992 | Corrigan et al. ............ 73/23.36 |
| 5,138,889 A | 8/1992 | Conrad | |
| 5,157,261 A | 10/1992 | Grey et al. | |
| 5,296,380 A | 3/1994 | Margalit | |
| 5,445,795 A * | 8/1995 | Lancaster et al. ............. 422/86 |
| 5,476,794 A | 12/1995 | O'Brien et al. | |
| 5,480,612 A | 1/1996 | Margalit | |
| 5,648,047 A | 7/1997 | Kardish et al. | |

(Continued)

FOREIGN PATENT DOCUMENTS

JP   9-126965   5/1997

(Continued)

*Primary Examiner*—Jill Warden
*Assistant Examiner*—Neil Turk
(74) *Attorney, Agent, or Firm*—Diederiks & Whitelaw PLC

(57) ABSTRACT

A fully integrated portable screening system includes a main housing and a contact pad. The contact pad is removably positioned in the main housing and covered by at least one sample sheet. The contact pad is preferably constituted by a cylindrical baton which carries a roll of sample collection sheets. A test subject interacts with the contact pad, leaving a trace sample on the sample collection sheet. The contact pad is then placed within the main housing and the trace sample is exposed to a test medium designed to interact with a specific analyte of interest potentially present in the trace sample. After exposure to the test medium, the sample sheet is subjected to a testing mechanism which exposes any interaction between the test medium and the analyte of interest to produce a test result.

15 Claims, 7 Drawing Sheets

U.S. PATENT DOCUMENTS

| | | |
|---|---|---|
| 5,741,984 A | 4/1998 | Danylewych-May et al. |
| 5,859,375 A | 1/1999 | Danylewych-May et al. |
| 6,446,514 B1 | 9/2002 | Danylewych-May et al. |
| 6,613,576 B1 | 9/2003 | Rodacy et al. |
| 6,914,668 B2 | 7/2005 | Brestel et al. |
| 7,047,829 B2 | 5/2006 | Napoli |
| 7,294,306 B2 * | 11/2007 | Haas et al. .................. 422/58 |
| 2004/0265169 A1 | 12/2004 | Haas et al. |
| 2005/0101027 A1 | 5/2005 | Haas |
| 2005/0287036 A1 | 12/2005 | Eckels et al. |

FOREIGN PATENT DOCUMENTS

| | | |
|---|---|---|
| WO | WO 2004/104559 | 12/2004 |

* cited by examiner

FULLY INTEGRATED PORTABLE SCREENING SYSTEM

CROSS-REFERENCE TO RELATED APPLICATION

The present application claims the benefit of U.S. Provisional Patent Application Ser. No. 60/723,433 filed Oct. 5, 2005 entitled "Compact, Portable Screening System For Trace Threat Materials."

BACKGROUND OF THE INVENTION

1. Field of the Invention

The present invention pertains to the art of screening systems and, more particularly, to a fully integrated portable screening system capable of scanning for various analytes of interest, such as explosives and other trace compounds.

2. Discussion of the Prior Art

Since Sep. 11, 2001, protection against terrorist threats has become a national priority. This priority extends from the protection of government facilities inside the U.S. and abroad to the protection of private businesses and venues. Various types of threats have been postulated, including attacks using explosives, chemical and/or biological agents and nuclear and radiological agents (dirty bombs). The diversity of these threats has created a number of complex security challenges for national, state, and local governments, the transportation industry, private businesses, and even individuals. Total expenditures related to Homeland Security topped $100B in 2003 and billions more have been allocated in Federal, Supplemental Appropriations and State/Local spending. Increasingly, U.S. businesses are devoting more revenue to security systems, with total expenditures reaching tens of billions of dollars. Growth in the homeland security industry is expected to be vigorous over the next decade. Motivated by the wide diversity of potential threats and by the inadequacy of currently available systems, government investments in research and development are on the rise.

Of the various potential threats, explosives remain the number one choice of most terrorists. Indeed, many experts have noted that, in the case of terrorist activity, compelling statistical evidence indicates that bombs are a primary threat. The pernicious and prevalent nature of this threat has been observed in recent attacks on military, civilian and private sector targets. In particular, bombs, or improvised explosive devices (IEDs), have become a major threat to U.S. military operations. IED attacks against U.S. and coalition led forces in Iraq have been responsible for more military and civilian casualties than any other single weapon. The diversity, deadliness and increasingly prevalent use of IEDs in such conflicts highlight the low risk and high payoff nature of the weapon. Notably, most of the currently proposed methods for combating this threat involve systems that attempt to detect the IED after deployment. This is the least optimum time to deal with the threat as the signature of the IED and the vulnerability of the enemy is never lower than after the IED has been deployed. Further, the technical demands on such systems are increasingly high, environmental clutter creates unacceptably high false alarm rates. Moreover, once an IED is deployed, the probability of detection must be near perfect. Thus, there is a compelling need for systems that can detect bombers, bomb makers and bomb making factories in these diverse settings prior to the deployment of the weapon. In order to be most effective, the systems should be portable, inexpensive and easy to use.

Most currently available explosive detection methods involve costly, large, fixed base and low throughput systems. Current systems can cost more than one million dollars per portal for bulk explosive detection and tens of thousands of dollars for trace explosive detection. Indeed, these systems are so costly and operator intensive that they are of limited utility for widespread distributed operations and are therefore most often used at choke points or portals. Existing and recently developed systems, which were designed to increase portability, are expensive and power intensive. Perhaps more importantly, these systems were not designed with the primary purpose of detecting bombers, bomb makers and bomb making factories, the detection of which would have a far greater impact on the overall use of IEDs than finding any single device.

Existing systems are designed to detect vapor emanating from explosives or traces of explosives rather than the direct detection of explosive particulates. As explosives have very low vapor pressures, the vapor signature emanating from an explosive can be exceedingly small thus driving systems to ultra-high sensitivity requirements which result in significant false alarm rates. In some cases, heating is required to create an increased vapor signature. In order to identify bombers and bomb makers, a detection system should be focused on sampling methods that maximize the probability of identifying individuals that have been in extensive contact with explosives or in explosive contaminated areas.

In summary, currently available screening systems, in particular, explosive screening systems, suffer from many disadvantages, such as high cost, low throughput, high false alarm rates, operational complexity high maintenance and training requirements, poorly designed sampling methods, high power requirements and the like. In addition, these systems are most typically designed to identify the bomb itself, not the bombers or the bomb maker. They are expensive and cumbersome, thereby not being well-suited for deployment in a wide variety of field settings. These limitations have created a significant barrier to conducting widespread explosive screening which is necessary to combat the threat.

Based on the above, there is a great and urgent need for a deployable, portable and low cost screening system having a sampling system designed to detect trace contamination on people and objects associated with certain people, while being capable of use in a variety of field settings.

SUMMARY OF THE INVENTION

The present invention is directed to a fully integrated portable screening system for detecting analytes of interest on individuals or objects. The screening system includes a main housing and a contact pad. The contact pad is removably positioned in the main housing and covered by at least one sample collection sheet. The contact pad is preferably constituted by a cylindrical baton which carries a roll of individual, single use sample collection sheets. In any event, after a subject either, an individual or an object, interacts with the contact pad, leaving a trace sample on the sample collection sheet, the contact pad is placed within the main housing and the trace sample is exposed to a test medium designed to interact with a specific analyte of interest potentially present in the trace sample. After exposure to the test medium, the sample sheet is subjected to a testing sequence which exposes any interaction between the test medium and the analyte of interest to produce a test result.

In accordance with the testing sequence of the invention, the test medium, preferably in the form of a photoluminescent compound, is sprayed onto the sample collection sheet. The photoluminescent compound is formulated to interact with, for example, explosive residue or another analyte of interest. When exposed to light at particular wavelengths, the analyte of interest either quenches luminescence or becomes luminescent. One, two or more distinct test mediums can be sprayed individually or sequentially onto the sample collection sheet depending upon the particular analyte(s) of interest. After exposing the sample collection sheet to the test medium (s), the operator simply activates a test mechanism and peers through a view port provided on the main housing to determine whether an analyte of interest is present in the trace sample.

In further accordance with the invention, the portable screening system includes a cueing system that indicates a need for system calibration. More specifically, periodically, such as after conducting a predetermined number of tests, the cuing system alerts the operator that the device should be calibrated. In the most preferred embodiment of the invention, one of the sample sheets includes a marker indicating a need for system calibration. That is, the sample sheets are provided on a roll or sheet feeder that allows continued use of the screening system. The roll of sample sheets is provided in a disposable sheath that protects the sample sheets from contamination and also enables operators to readily re-load additional sample sheets into the threat screening system while in the field. In any event, as sample sheets are used, the roll diminishes and one of the sheets is provided with a visual marker indicating a need for calibration. For example, one in every one hundred sample sheets can include the visual marker. During calibration, a test strip or calibration pen/marker containing the analyte of interest is applied to the sample sheet and subjected to the scanning process to ensure that the system is operating properly.

Additional objects, features and advantages of the present invention will become more readily apparent from the following detailed description of preferred embodiments when taken in conjunction with the drawings wherein like reference numerals refer to corresponding parts in the several views.

DETAILED DESCRIPTION OF THE PREFERRED EMBODIMENTS

Figure 1:
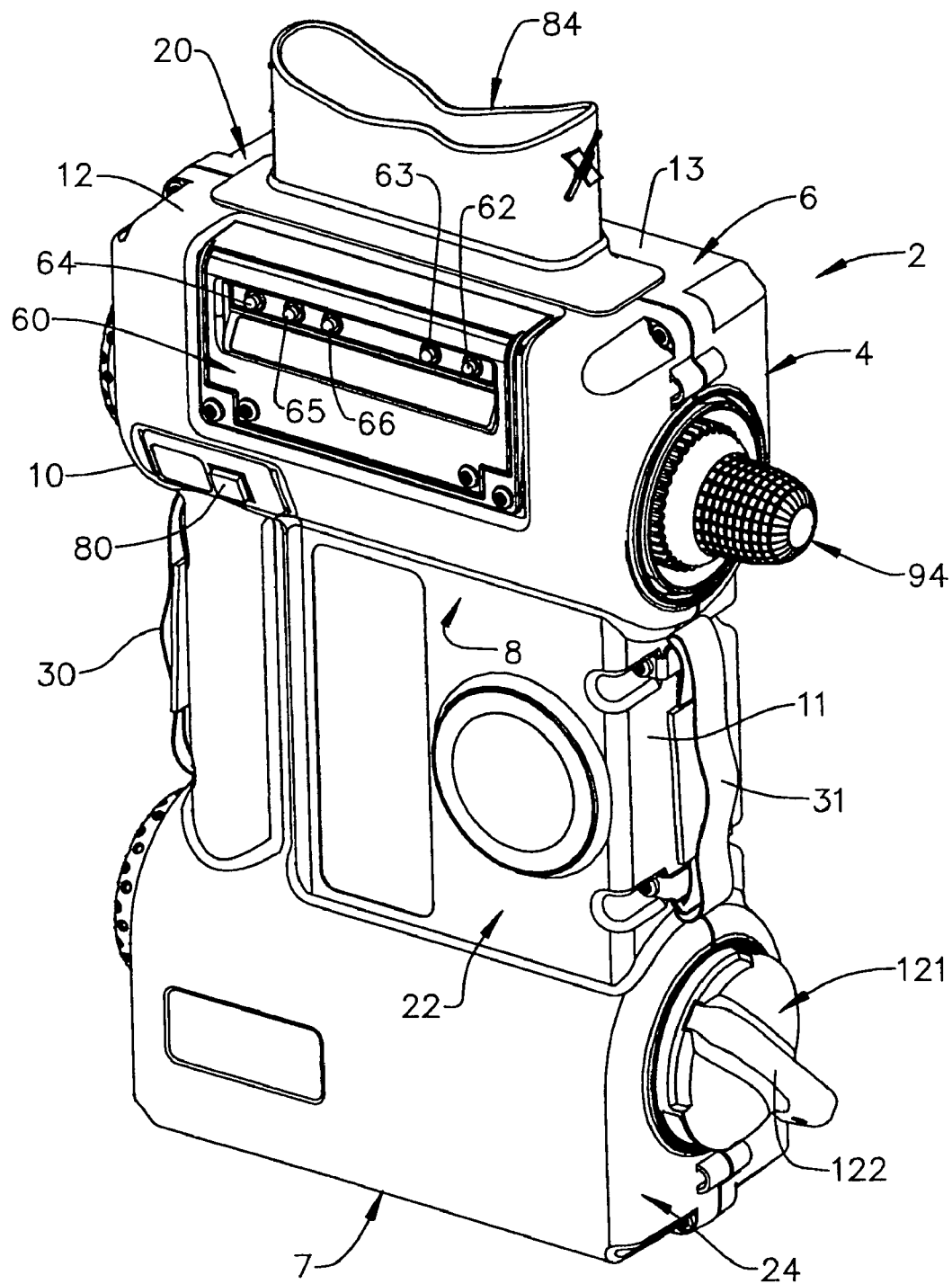
FIG. 1 is a front right perspective view of a fully integrated portable screening system constructed in accordance with the present invention.
Figure 2:
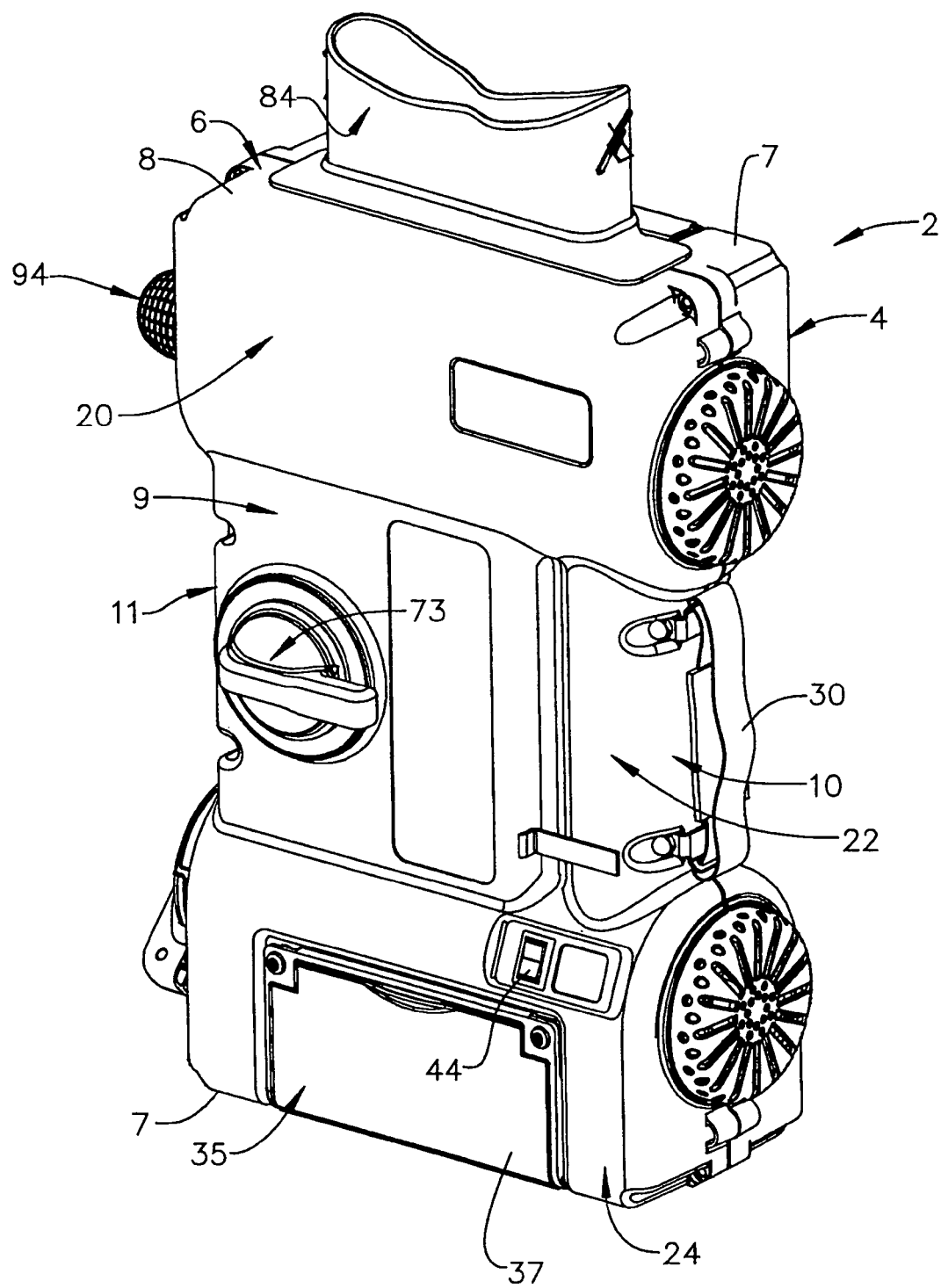
FIG. 2 is a rear perspective view of the screening system of FIG. 1.
Figure 3:
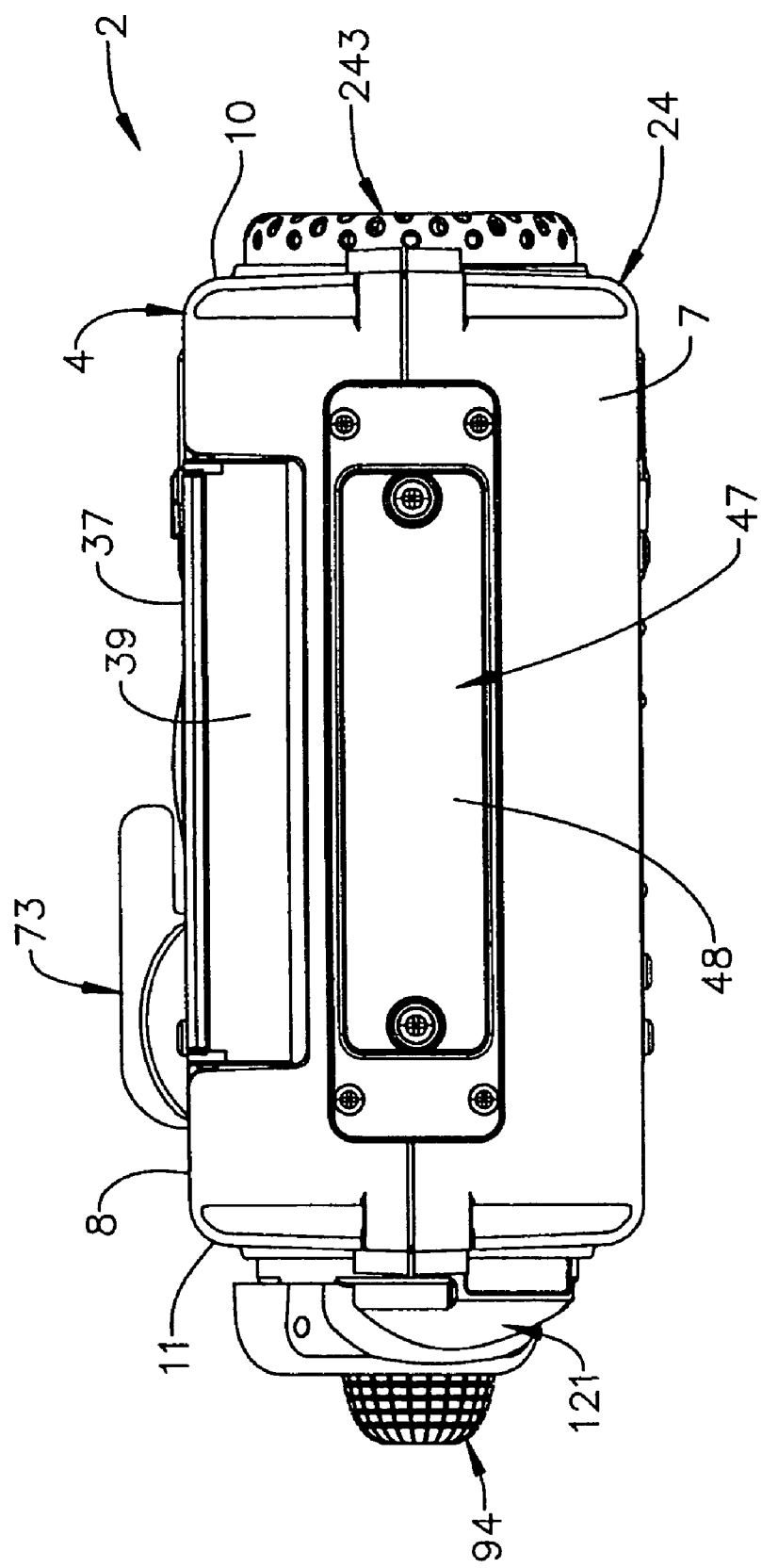
FIG. 3 is a bottom view of the screening system of FIG. 1.

With initial reference to FIGS. 1-3, a self contained, fully integrated, portable screening system for determining whether a subject has been in contact with a particular analyte of interest is generally indicated at 2. By portable, it should be understood that the present invention is a small (no larger than a briefcase) light unit that is readily transportable and deployable by a single individual operator. In any event, screening system 2 includes a main housing 4 having a top wall 6, a bottom wall 7, a front wall 8, a rear wall 9 and opposing side walls 10 and 11. Actually, main housing 4 is formed from first and second housing halves 12 and 13 that are joined through a plurality of mechanical fasteners (not separately labeled) arranged at various locations along top, bottom, and opposing walls 6, 7, 10 and 11. Main housing 4 is basically divided into three zones, namely an upper zone 20, an intermediate zone 22 and a lower zone 24. As will be detailed more fully below, upper zone 20 contains a sample collection device, intermediate zone 22 includes a reagent application system and lower zone 24 provides storage and internal access zones for screening system 2. In any event, first and second handles 30 and 31 are provided on opposing side walls 10 and 11 to enable an operator to readily grasp and operate portable screening system 2.

Figure 6:
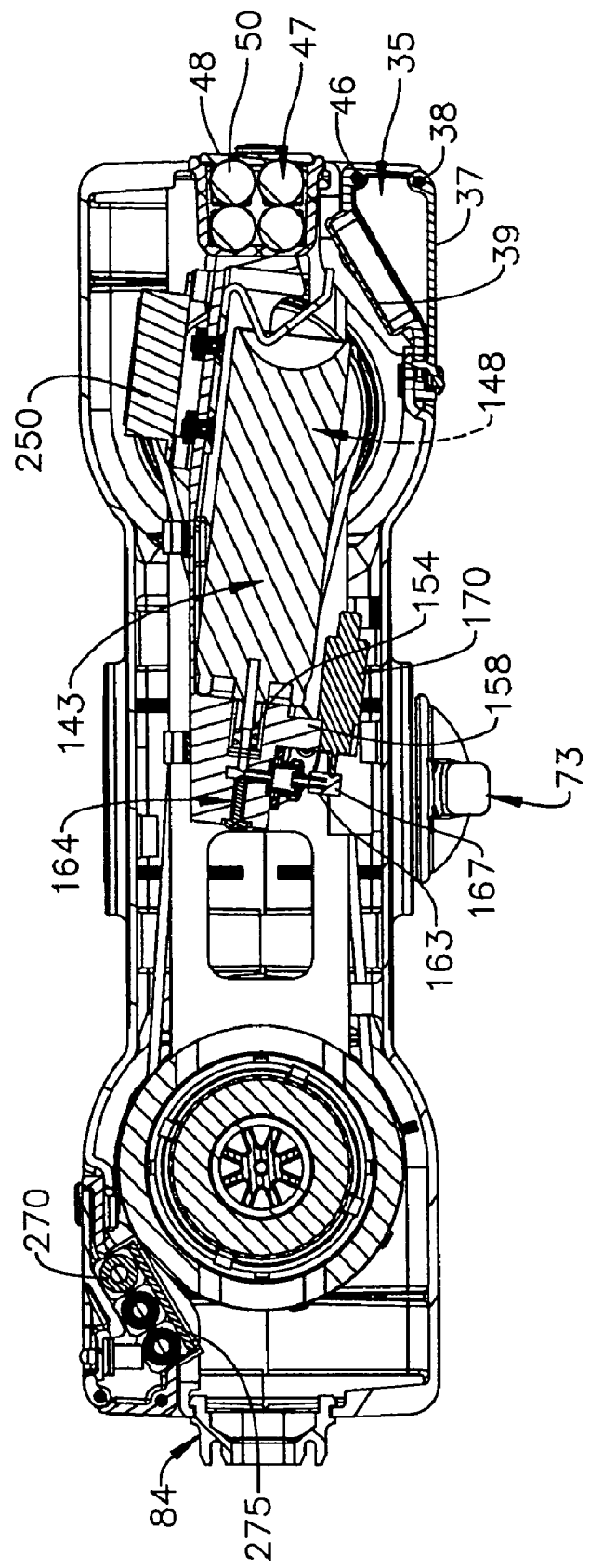
FIG. 6 is a left side, cut-away view of the portable screening system.

As best shown in FIGS. 2 and 6, screening system 2 is provided with a toolbox 35 that can preferably house various tools or other items, such as a screwdriver, a lens cleaning cloth, calibration media and the like. Toolbox 35 includes a cover 37 that is hingedly mounted to rear wall 9 through a hinge element 38 (FIG. 6). Below cover 37 is a second or reagent access cover 39 that is pivotally mounted to bottom wall 7 through a hinge element 46. As will be discussed more fully below, reagent access cover 39 is selectively opened to replenish reagent in intermediate zone 22. Arranged above toolbox 35 is a power switch 44 and below toolbox 35, on bottom wall 7, is arranged a battery compartment 47 (see FIGS. 3 and 6). Battery compartment 47 includes a battery cover 48 that selectively provides access to a plurality of batteries, one of which is indicated at 50 in FIG. 6, which provide the necessary power for screening system 2.

Referring back to FIG. 1, screening system 2 includes an indicator panel 60 provided on front wall 8. Indicator panel 60 includes a plurality of LEDs 62-66 that provide visual information to the operator. For example, LED 62 is illuminated to indicate when power is on, LED 63 is illuminated to provide a low battery warning and indicator lights 64-66 are associated with particular reagents or test mediums being employed to test a sample. As will be discussed more fully below, in order to choose a particular reagent, an operator rotates a selector switch 73 (see FIG. 2) provided on rear wall 9. In a manner that will also be discussed more fully below, following application of the medium, the operator activates a view switch 80 provided on front wall 8 to activate a testing mechanism which reveals a test result. Preferably, the operator peers through a view finder 84 in order to view the test result.

Figure 4:
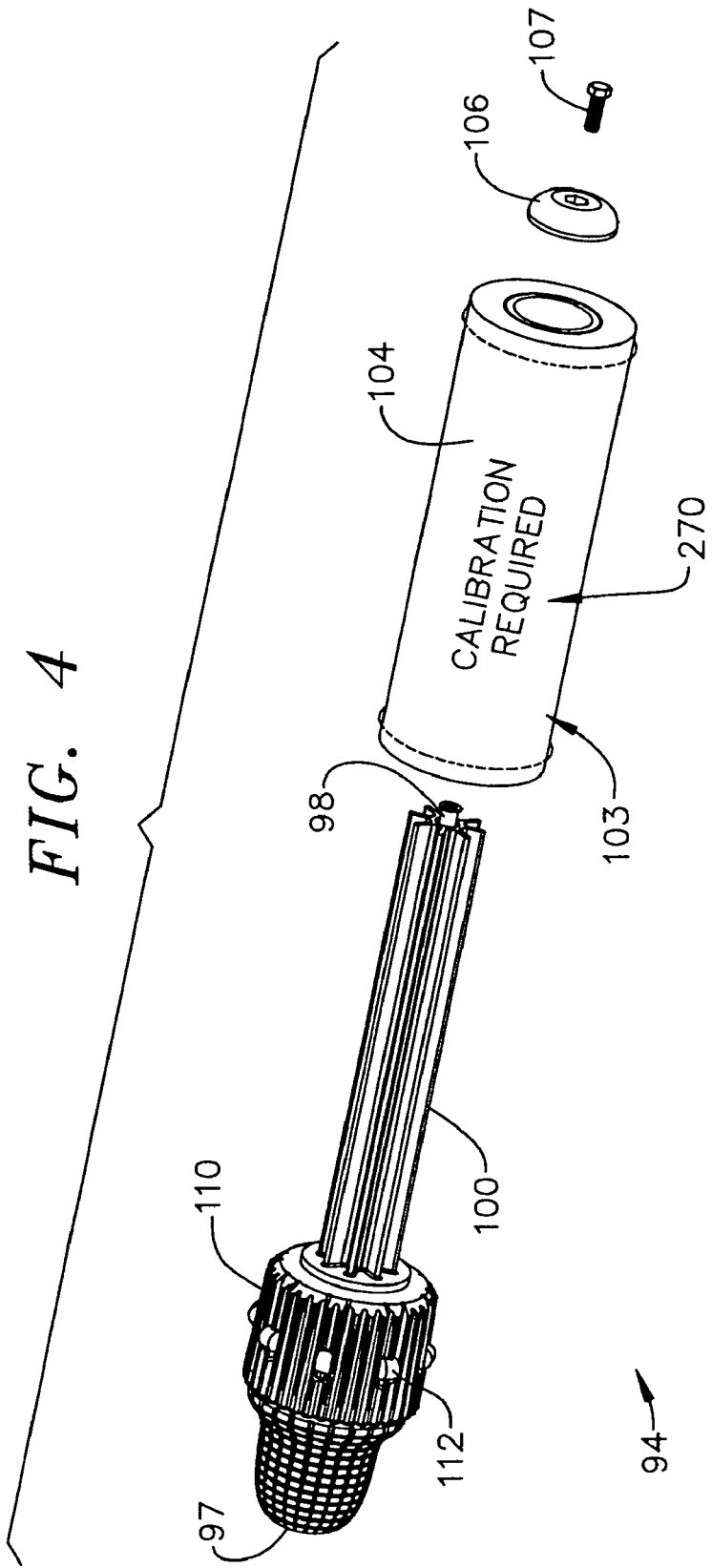
FIG. 4 is an exploded view of a contact pad shown in the form of a baton employed in connection with the screening system constructed in accordance with the present invention.

In accordance with the invention, portable screening system 2 employs a contact pad or baton 94 to obtain a trace sample which potentially contains an analyte of interest from a subject. To obtain a sample, an individual is asked to grasp baton 94, alternatively, baton 94 can be rolled or brushed across an object to obtain a trace sample. As best shown in FIG. 4, baton 94 includes a first end or handle 97 that extends to a second end 98 through an intermediate portion or media core 100. Media core 100 is designed to snuggly receive a sample collection sheet roll 103 which includes a plurality of individual single collection sheets, one of which is indicted at 104, secured to baton 94 through use of a clamping unit such as a washer 106 and a mechanical fastener 107. After each screening, the used sample collection sheet is removed to expose a new, pristine sample collection sheet 104 for a subsequent testing procedures. Preferably, each sample collection sheet 104 is coated with a tacky adhesive that retains trace residue and any potential analytes of interest obtained from the subject. In addition, each sample collection sheet can be provided with a surfactant or catalyst, such as zinc powder, is that enhances analyte detection. In any case, baton 94 includes an interface section 110 arranged proximate to handle 97. Interface section 110 is preferably provided with a plurality of spring clips 112 which, as will be discussed more fully below, engage a sheath 115 (FIG. 5) provided in upper zone 20 of portable screening system 2. Sheath 115 is operatively associated with a crank handle 121 having a gripping portion 122. Crank handle 121 is rotated following a sample collection stop to activate an operating mechanism 125 to initiate a screening process.

Figure 5:
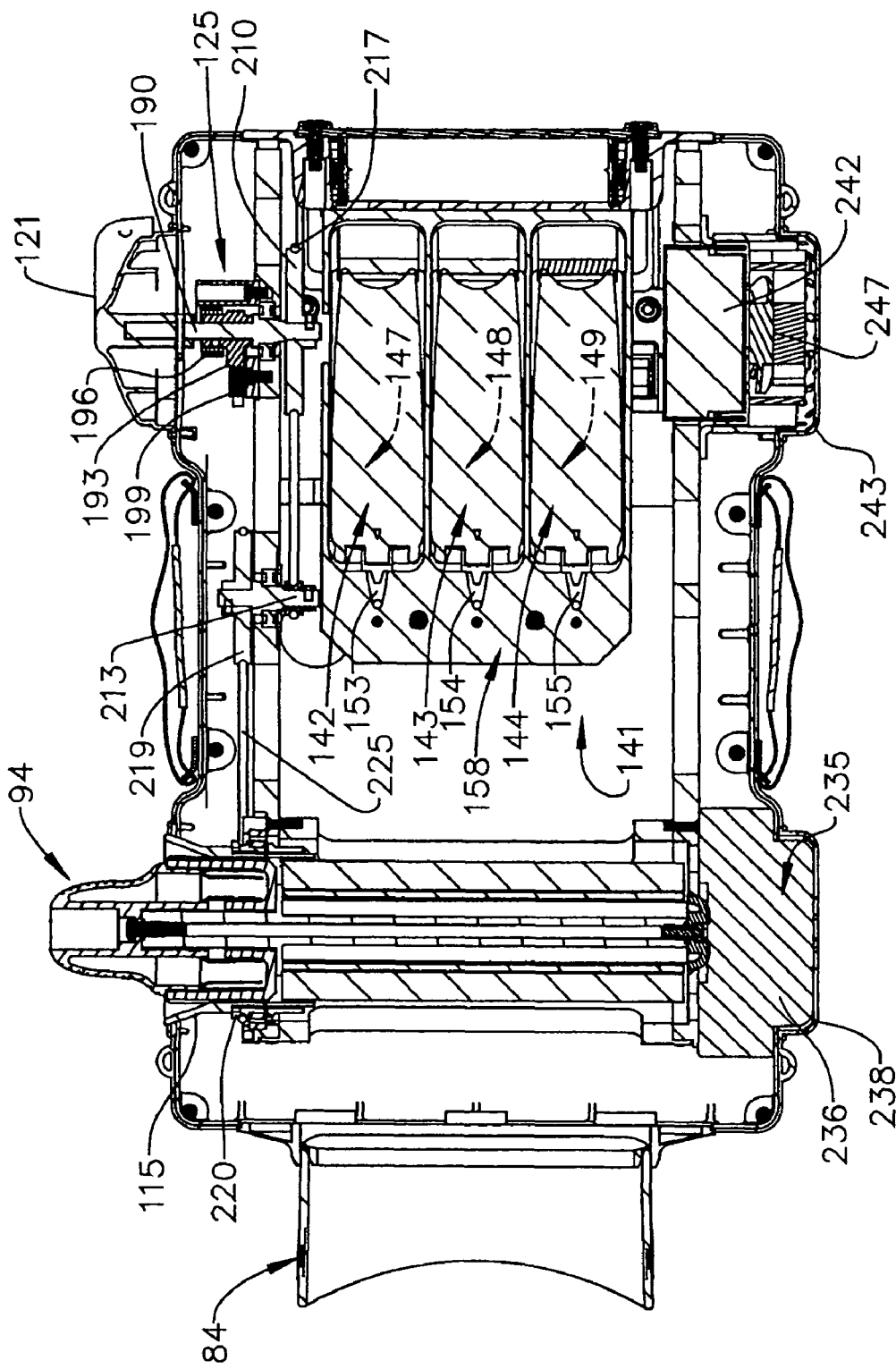
FIG. 5 is a cut-away view illustrating internal components of the portable screening system constructed in accordance with the present invention.

In further accordance with the invention, after obtaining a trace sample from a test subject, the sample collection sheet is exposed to a test medium(s) or activating solution(s) which is formulated to interact with particular analytes of interest. As best shown in FIGS. 5 and 6, portable screening system 2 includes a reagent or solution application system 141 arranged substantially within intermediate zone 22. Application system 141 includes a plurality of solution containers 142-144 which store one or more test mediums under pressure. Containers 142-144 are inserted into intermediate zone 22 through reagent access cover 39. In any event, the test medium is preferably a photoluminescent compound which is converted to aerosol form and delivered onto sample collection sheet 104. More specifically, each solution container 142-144 includes a corresponding receptacle or containing portion 147-149 that stores a test medium in liquid form and an outlet or primary valve 153-155 that is fluidly connected to a central manifold 158. Central manifold 158 includes a secondary valve 163 controlled by a metering pin 164. Metering pin 164 controls how much test medium is directed through a nozzle 167. In order to choose from which container the test medium is released, the operator selectively rotates selector switch 73 to a desired position which corresponds to one of containers 142-144.

More specifically, nozzle 167 is operatively associated with a solenoid 170 that, upon receiving a dispensing command, opens secondary valve 163 causing the test medium to exit from nozzle 167 in an atomized or aerosol form, with the spray being directed onto sample collection sheet 104. Preferably, the spray of solution is cone-shaped having a base diameter of approximately three inches or more. In this manner, sample collection sheet 104 is substantially, completely coated with test medium. In order to more completely coat sample collection sheet 104 with test medium, baton 94 is rotated during the spraying operation.

In still further accordance with the invention, after inserting baton 94 into sheath 115, view switch 80 blinks red to indicate that sample collection sheet 104 is positioned and ready for the application of test medium. Towards that end, the operator rotates crank handle 121 to initiate operating mechanism 125. Operating mechanism 125 includes a rotary shaft 190 operatively connected to crank handle 121. Rotary shaft 190 extends through and is connected with a cam unit 193 and a torsion spring 196. Cam unit 193 includes a cam lobe (not labeled) that engages a switch 199 configured to activate solenoid 170 to release the test medium onto sample collection sheet 104. More specifically, after rotating crank handle 121 approximately one-quarter turn to load torsion spring 196, gripping portion 122 is released causing crank handle 121 to return to a home or initial position through application of a biasing force supplied by torsion spring 196. As crank handle 121 returns to the home position, rotary shaft 190 rotates cam unit 193, causing the cam lobe to engage with switch 199 and solenoid 170 to be activated in order to release the test medium onto sample collection sheet 104. As stated above, as the solution is released, baton 94 rotates within sheath 115, ensuring complete coverage of sample collection sheet 104 in a manner that will be detailed more fully below.

Figure 7:
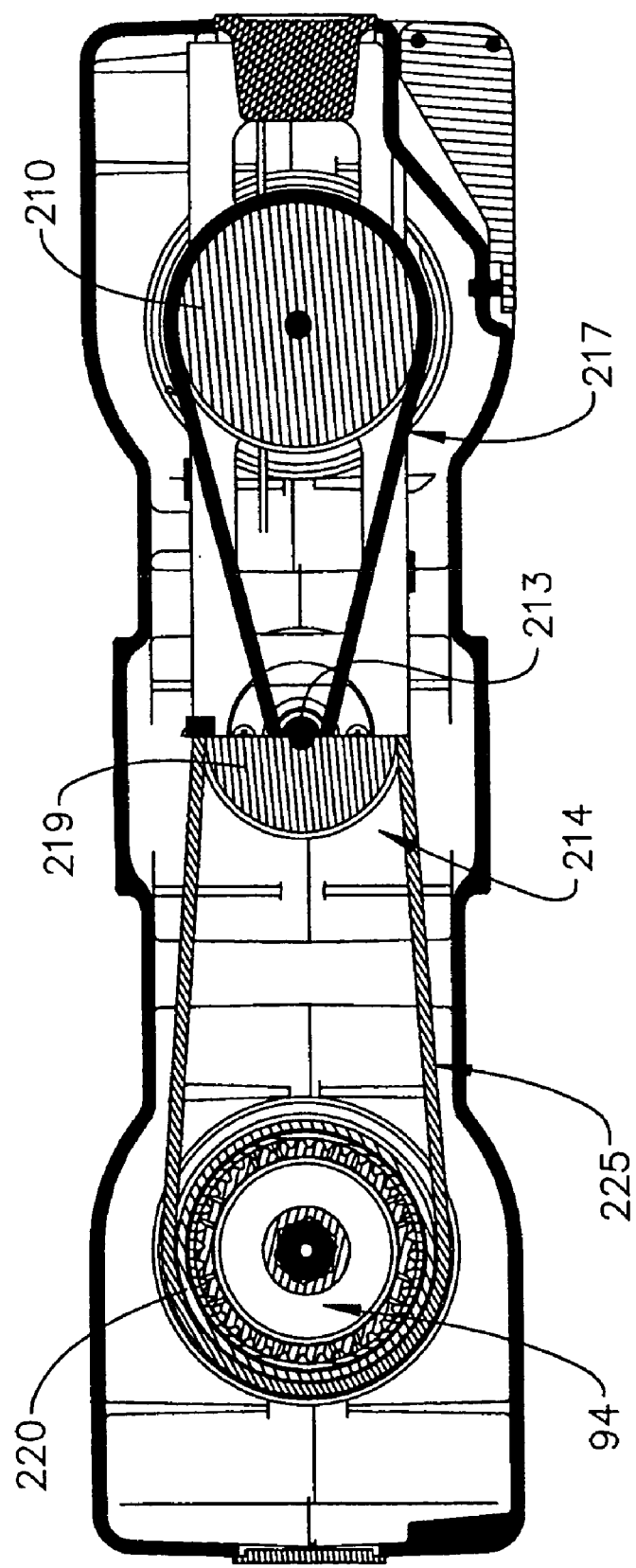
FIG. 7 is a left side cut-away view of the present invention illustrating an operating mechanism employed to simultaneously release a test medium and rotate the baton of FIG. 2 to ensure substantially complete coverage of a sample collection sheet.

As best shown in FIGS. 5 and 7, rotary shaft 190 is operatively connected to a first or drive pulley 210. Drive pulley 210 is connected to an inner hub 213 of a second pulley 214 by a first belt 217. An outer hub 219 of second pulley 213 is connected to a third or driven pulley 220 through a second belt 225. Third pulley 220 is coupled to interface section 110 of baton 94 through spring clips 112 such that any movement of third pulley 220 is directly transferred to baton 94. The preferred configuration provides a 4:1 ratio between drive pulley 210 and driven pulley 220. In this manner, one quarter turn of crank handle 121 results in one complete revolution of baton 94. Thus, releasing crank handle 121, as discussed above, not only results in activating switch 199 but also causes baton 94 to undergo one complete reverse revolution which ensures that sample collection sheet 104 is substantially fully coated with test medium.

Following application of the test medium, a dryer unit 235 is activated to rapidly dry sample collection sheet 104. Dryer unit 235 includes a fan 236 that directs air through an intake port 238 onto baton 94 to dry sample collection sheet 104. At this point, it should be noted that dryer unit 235 could employ a heater or a combination heater and fan to dry sample collection sheet 104. During operation of dryer unit 235, an exhaust fan 242, located in lower zone 24, is operated to guide air out from portable screening system 2 through an exhaust port 243. Prior to exiting exhaust port 243, exhaust air passes through a filter 247. Filter 247 employs charcoal or the like to remove foreign particles and/or residual test medium from the exhaust air. The operation of dryer unit 235 and exhaust fan 242 is established by a control board 250 which also provides a signal to the operator that sample collection sheet 104 is dry and the sample is ready for viewing.

More specifically, after sample collection sheet 104 is dry, view switch 80 changes from red to green indicating that the sample is ready for viewing. At this point, the operator peers through view finder 84 and presses view switch 80 to activate a testing mechanism, preferably in the form of a light source 270 most preferably in the form of an ultraviolet light source. Light source 270 passes through a UV filter lens 275 and bathes sample collection sheet 104 in light. Preferably, light source 270 is constituted by a 380 nm cold cathode tube. In any event, if the subject has handled or been in contact with the analyte of interest, the solution sprayed onto sample collection sheet 104 will cause trace particles of the analyte obtained from the subject to quench luminescence or create luminescence providing a test result that is viewed by the operator through view finder 84. Portable screening system 2 can be reconfigured to screen from numerous analytes of interest by simply changing light source 270 and/or the test medium.

At this point, it should be readily understood that the portable screening system constructed in accordance with the present invention provides for a simple, easily transportable method of testing individuals for contact with analytes of interest. In order to enhance detection levels, is portable screening system 2 can be readily calibrated at periodic intervals. For example, a visual cue 270 can be provided to the operator on, for example, one of sample sheets 104. As sample sheets are used, roll 103 diminishes and one of the sample sheets 104 provided with visual marker or cue 270 that becomes exposed. For example, one in every one hundred sheets can include visual cue 270. When cue 270 appears, the operator simply applies a calibration media containing the analyte of interest to the sample collection sheet. Once applied, the baton is inserted into sheath 115 and the sample sheet is analyzed in the manner described above. The results should indicate the presence of the test substance. If not, screening system 2 would require servicing. Visual cue 270 could also be presented as a separate LED on indicator panel 60.

In any case, the portable screening system of the present invention enables rapid and accurate scanning of numerous individuals and objects under field conditions without requiring expensive support systems typically required. Although described with reference to a preferred embodiment of the invention, it should be readily understood that various changes and/or modifications can be made to the invention without departing from the spirit thereof. For instance, the portable screening system can be incorporated into a briefcase-like device with contact pad 97 being substantially planar. In addition, various light sources employing different wavelengths can be employed depending on the particular analytes of interest and/or test medium. For that matter, the test medium can be varied depending upon the particular analyte of interest. Furthermore, the application process can be varied to release one or more diverse test mediums sequentially or simultaneously depending upon current circumstances. In general, the invention is only intended to be limited by the scope of the following claims.

We claim:

1. A fully integrated portable screening system for detecting analytes of interest comprising:
    a main housing;
    a contact pad removably positioned in the main housing, said contact pad including a sample sheet for collecting a trace sample from a test subject;
    at least one container positioned within the main housing;
    a test medium carried within the at least one container and adapted to interact with an analyte of interest present in the trace sample;
    an application system operatively connected to the at least one container, said application system selectively directing the test medium onto the sample sheet;
    a testing mechanism including a light source mounted in the housing proximate to the sample sheet, said testing mechanism interacting with the test medium and the trace sample to produce a test result; and
    a view port provided in the housing and exposed to the contact pad, said view port allowing an operator of the portable screening device to view the test result.

2. The portable screening system according to claim 1, further comprising: an operating mechanism for selectively activating the application system.

3. The portable screening system according to claim 2, wherein the contact pad constitutes a cylindrical baton including an interface section and a handle adapted to be gripped by a user, wherein the interface section is removably housed within said main housing, said sample sheet being wrapped about the interface section of the cylindrical baton.

4. The portable screening system according to claim 3, wherein the operating mechanism is mechanically linked to the baton.

5. The portable screening system according to claim 4, wherein the operating mechanism includes a first pulley connected to a second pulley through a first belt, said second pulley being connected to a third pulley through a second drive belt, said third pulley being linked to the baton.

6. The portable screening system according to claim 2, wherein the operating mechanism includes:
    a switch operatively connected to the application system; and
    a cam member operatively connected to a switch, said cam member being adapted to operate the switch to direct the test medium onto the sample collection sheet.

7. The portable screening system according to claim 2, wherein the at least one container includes multiple containers each including an outlet operatively connected to a manifold having a valve.

8. The portable screening system according to claim 7, further comprising: a selector switch operatively connected to the application system, said selector switch being adapted to select from which of the multiple containers the test medium is released.

9. The portable screening system according to claim 7, further comprising: a nozzle fluidly connected to the manifold, said nozzle being adapted to direct a conical spray of test medium onto the sample sheet upon operation of the application system.

10. The portable screening system according to claim 1, further comprising: a cueing system including at least one indicator that signals a need for a calibration process.

11. The portable screening system according to claim 1, wherein the test medium is constituted by a photoluminescent solution adapted to react with a particular analyte of interest potentially present in the trace sample.

12. The portable screening system according to claim 11, wherein the light source is directed onto the contact pad, said light source being adapted to reveal the test result.

13. The portable screening system according to claim 12, wherein the light source is constituted by an ultraviolet light, said ultraviolet light being adapted to cause the analyte of interest to luminesce or quench luminescence when subjected to the test medium.

14. The portable screening system according to claim 13, wherein the ultraviolet light has a wavelength of 380 nm.

15. The portable screening system according to claim 1, further comprising: a drying system arranged in the main housing, said drying system being adapted to dry the sample sheet following application of the test medium.

* * * * *